(12) United States Patent
Patel

(10) Patent No.: US 9,606,078 B2
(45) Date of Patent: Mar. 28, 2017

(54) NANOCRYSTALLINE INDUM TIN OXIDE SENSORS AND ARRAYS

(75) Inventor: Nirmalkumar G. Patel, Jacksonville, FL (US)

(73) Assignee: University of North Florida Board of Trustees, Jacksonville, FL (US)

(*) Notice: Subject to any disclaimer, the term of this patent is extended or adjusted under 35 U.S.C. 154(b) by 1369 days.

(21) Appl. No.: 11/938,290

(22) Filed: Nov. 11, 2007

(65) Prior Publication Data

US 2010/0279425 A1    Nov. 4, 2010

(51) Int. Cl.
| | | |
|---|---|---|
| G01N 33/68 | (2006.01) | |
| G01N 27/12 | (2006.01) | |
| G01N 33/00 | (2006.01) | |

(52) U.S. Cl.
CPC .................... G01N 27/125 (2013.01)

(58) Field of Classification Search
CPC .................................................... G01N 27/125
USPC ............................................ 436/149; 422/98
See application file for complete search history.

(56) References Cited

U.S. PATENT DOCUMENTS

| | | | |
|---|---|---|---|
| 4,822,465 A | 4/1989 | Jones et al. | |
| 4,906,440 A | 3/1990 | Kolesar, Jr. | |
| 4,969,956 A | 11/1990 | Kreider et al. | |
| 5,520,787 A | 5/1996 | Hanagan et al. | |
| 5,571,401 A | 11/1996 | Lewis et al. | |
| 5,591,321 A | 1/1997 | Pyke | |
| 7,254,986 B2* | 8/2007 | Stokes et al. | ................ 73/31.06 |

(Continued)

*Primary Examiner* — Rebecca M Fritchman
(74) *Attorney, Agent, or Firm* — Molly L. Sauter; Nilay J. Choksi; Smith & Hopen, P.A.

(57) ABSTRACT

A sensor for sensing gaseous chemicals includes a substrate, a variable resistance nanocrystalline ITO thin film formed on the substrate, and electrodes electrically coupled to the thin film. A sensor array assembly includes a sensor slide and a perforated interface circuit. The interface circuit abuts and electrically couples the sensor slide. The sensor slide includes several spaced apart ITO film strips formed on a slide substrate. A common electrode is electrically coupled to a common portion of each ITO film strip providing an electrically conductive path across the common portions of each of the plurality of spaced apart ITO film strips. A discrete electrode is electrically coupled to a discrete portion of each ITO film strip. The interface circuit is configured to abut and electrically couple to the sensor slide. A conductive discrete electrode pad electrically couples each of the plurality of discrete electrodes of the sensor slide to discrete terminals on the interface circuit. A conductive common electrode pad is associated with and electrically couples the common electrode of the sensor slide to a common electrode on the interface circuit. Apertures in the interface circuit expose the thin film to the environment. Resistance changes in a detectible manner upon exposure to sensible chemicals at ambient temperature, such as 1,2,2-Trimethylpropyl methylphosphonofluoridate (soman, GD), O-Ethyl S-(2-isopropylaminoethyl) methylphosphonothiolate (VX), distilled bis(2-chloroethyl) sulfide (mustard, HD), carbonyl chloride, Phosgene (CG) and cyanogen chloride (CK), ozone, carbon monoxide, carbon dioxide, acetylene, propane, ammonia, sulfur dioxide, ethanol, methanol, volatile organic compounds and industrial toxic chemicals.

13 Claims, 21 Drawing Sheets

(56) References Cited

U.S. PATENT DOCUMENTS 7,470,533 B2 * 12/2008 Xu et al. .................. 435/285.2
2003/0215865 A1   11/2003 Mayer et al.
2005/0258051 A1   11/2005 Ono et al.
2007/0127164 A1    6/2007 Ofek et al.

* cited by examiner

Calibration of ITO Gas Sensor with Soman (GD)

$y = 0.0002x - 0.0256$
$R^2 = 0.9874$

%Sensitivity, S vs Concentration of GD, ppm

FIGURE 14

Calibration of ITO Gas Sensor with VX

NANOCRYSTALLINE INDUM TIN OXIDE SENSORS AND ARRAYS

GOVERNMENT LICENSE RIGHTS

The U.S. Government has a paid-up license in this invention and the right in limited circumstances to require the patent owner to license others on reasonable terms as provided for by the terms of DOD W911 SR-04-C-0072, awarded by the United States Army.

FIELD OF THE INVENTION

This invention generally relates to detection of chemical warfare agents, and, more particularly, to portable sensors for detecting a wide range of chemical warfare agents rapidly in ambient conditions.

BACKGROUND

As chemical warfare agents pose an ever increasing risk, an urgent need exists for reliable sensors. Ideally, a sensor would be portable and operate in ambient conditions to reliably detect a wide variety of chemical warfare agents (CWA) with exceptional sensitivity, selectivity and response time. In addition, the resulting system must be rugged, cost effective and of simple design, such that it may readily be deployed in any environmental setting. Particularly problematic for conventional sensors are the requirements for response time and sensitivity in ambient conditions.

Among the many chemical warfare agent of special interest to counterterrorism and military personnel are nerve, blister and pulmonary agents. Nerve agents include organophosphorous compounds, such as 1-Methylethyl methylphosphonofluoridate (sarin, GB); 1,2,2-Trimethylpropyl methylphosphonofluoridate (soman, GD); Cyclohexyl methylphosphonofluoridate (GF), Ethyl dimethylphosphoramidocyanidate (tabun, GA), and O-Ethyl S-(2-isopropylaminoethyl) methylphosphonothiolate (VX). Blister agents include organosulfur compounds, such as distilled bis(2-chloroethyl) sulfide (mustard, HD). Pulmonary agents include acid chlorides, such as phosgene (CG) and blood agents such as cyanogen chloride (CK).

A number of techniques for CWA detection have been investigated. These include gas chromatography (GC), liquid chromatography (LC), mass spectrometry, nuclear magnetic resonance (NMR) and Fourier transform infrared (FTIR) spectroscopy. Sensors based on thermoelectric effect, fiber optic/surface plasmon, solid state electrochemical, MOS devices, surface acoustic wave, and others have been devised. While such technologies may be effective for CWA detection, none have the desired aggregate characteristics, as described above.

What is needed is a cost-effective, rugged, easy to use, portable sensor system that operates in ambient conditions and without need of an external or integrated heater and also reliably detects a wide variety of chemical warfare agents (CWA) with exceptional sensitivity, selectivity and response time. The invention is directed to overcoming one or more of the problems and solving one or more of the needs as set forth above.

SUMMARY OF THE INVENTION

To solve one or more of the problems set forth above, in an exemplary implementation of the invention, a sensor for sensing gaseous chemicals is provided. The sensor comprises a substrate, a nanocrystalline ITO thin film formed on the substrate may have a variable electrical resistance affected by exposure to a sensible gaseous chemical, a first electrode electrically coupled to a first portion of the thin film; and a second electrode electrically coupled to a second portion of the thin film, the second portion being spaced apart from the first portion. The nanocrystalline ITO thin film may have a thickness of 500 to 4000 Å and an average grain size of 20 to 80 nm. The nanocrystalline ITO thin film may have a rectangular strip shape with a first end and an opposite second end, the first portion of the thin film being at the first end, and the second portion of the thin film being at the second end. The first electrode and the second electrode may be operably coupled to a device configured to monitor electrical resistance across the nanocrystalline ITO thin film over time. Significantly, the sensor operates at ambient temperature without requiring a heater, such as an external or integrated heater.

The device may optionally include an analog to digital converter configured to convert received analog electrical resistance signals to monitored digital resistance data, a storage means for storing the monitored digital resistance data as well as electrical resistance data characteristic of determined chemicals, and means for comparing monitored digital resistance data with electrical resistance data characteristic of determined chemicals.

In another aspect of the invention, a sensor assembly for sensing gaseous chemicals is provided. The sensor assembly comprises a sensor slide and an interface circuit. The interface circuit may be a printed circuit board. The interface circuit is configured to abut and electrically couple to the sensor slide. The sensor slide comprises a slide substrate, a plurality of spaced apart ITO film strips formed on the slide substrate, each ITO film strip having a variable electrical resistance affected by exposure to a sensible gaseous chemical. The slide substrate may comprise a material from the group consisting of glass, alumina, silicon, and silicon dioxide. Each ITO film strip may have a common portion and a discrete portion spaced apart therefrom. A common electrode is electrically coupled to the common portion of each ITO film strip providing an electrically conductive path across the common portions of each of the plurality of spaced apart ITO film strips. A discrete electrode is electrically coupled to the discrete portion of each ITO film strip. The common electrode and discrete electrodes may comprise gold. The interface circuit comprises a circuit substrate, at least one conductive common electrode pad and a common electrode terminal. The conductive common electrode pad is associated with and electrically coupled to the common electrode terminal. A plurality of conductive discrete electrode pads and a plurality of discrete electrode terminals are also provided. Each conductive discrete electrode pad is associated with and electrically coupled to one of the plurality of discrete electrode terminals. The interface circuit is configured to abut and electrically couple to the sensor slide. Each conductive common electrode pad is associated with and electrically couples each of the plurality of discrete electrodes of the sensor slide. The conductive common electrode pad is associated with and electrically couples the common electrode of the sensor slide. The plurality of spaced apart ITO film strips comprise nanocrystalline ITO thin film having a thickness of 500 to 4000 Å and an average grain size of 20 to 80 nm.

In another aspect of the invention, the interface circuit is perforated with a plurality of apertures. An aperture is configured to align with one of the plurality of spaced apart ITO film strips formed on the slide substrate when the interface circuit abuts and electrically couples to the sensor slide.

In another aspect of the invention, a conductive tape band is disposed between and configured to adhesively and conductively join each of the plurality of discrete electrodes of the sensor slide and the conductive common electrode pad associated with and electrically coupled thereto. Each conductive tape band is configured to absorb energy of sudden impulses. The conductive tape band being disposed between and configured to adhesively and conductively join each of the plurality of discrete electrodes of the sensor slide and the conductive common electrode pad associated with and electrically coupled thereto.

In another aspect of the invention, the common electrode terminal and the plurality of discrete electrode terminals are each operably coupled to a device configured to monitor electrical resistance across each ITO film strip over time. The plurality of spaced apart ITO film strips is configured to experience a determined change in resistance in a determined amount of time after exposure to a gaseous chemical warfare agent. The plurality of sensors forms an array.

In yet another aspect of the invention a method for sensing gaseous chemicals is provided. Sensors or arrays can detect gas or vapor at ambient temperature and do not need an external or integrated heater. The method entails providing a sensor as described above. Resistance across the nanocrystalline ITO thin film is monitored over time. The monitored resistance over time is compared with resistance data for determined chemicals. If monitored resistance over time matches resistance data for determined chemicals, then a determined chemical agent has been detected.

BRIEF DESCRIPTION OF THE DRAWINGS

The foregoing and other aspects, objects, features and advantages of the invention will become better understood with reference to the following description, appended claims, and accompanying drawings, where:

FIG. 14 is a chart that illustrates calibration of an ITO thin film sensor having a thickness of 2000 Å in the presence of soman vapor in accordance with principles of the invention; FIG. 18 is a chart that illustrates calibration of an ITO thin film sensor having a thickness of 1500 Å in the presence of VX vapor in accordance with principles of the invention.

Figure 1:
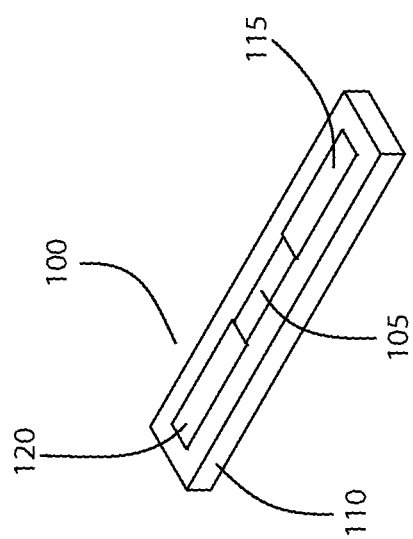
FIG. 1 shows a perspective view of an exemplary sensor according to principles of the invention.

Those skilled in the art will appreciate that the figures are not intended to be drawn to any particular scale; nor are the figures intended to illustrate every embodiment of the invention. The invention is not limited to the exemplary embodiments depicted in the figures or the arrangements, or the shapes, configurations, relative sizes, ornamental aspects, proportions, thicknesses, chemicals, concentrations, equations or steps shown in the figures.

DETAILED DESCRIPTION

Referring to the Figures, in which like parts are indicated with the same reference numerals, various views of an exemplary sensor and a sensor array according to principles of the invention are shown. In general, an exemplary sensor according to principles of the invention comprises a nanocrystalline indium tin oxide (ITO, or tin-doped indium oxide) thin film applied to a substrate. The indium tin oxide film comprises a mixture of indium(III) oxide ($In_2O_3$) and tin(IV) oxide ($SnO_2$), by way of example and not limitation 90% $In_2O_3$ and 10% $SnO_2$ by weight. The substrate is an electrical insulator that is compatible with the process of forming the ITO thin film. By way of example and not limitation, glass, alumina $Al_2O_3$, silicon, silicon dioxide $SiO_2$ or another compatible material may be utilized as the substrate. A pair of electrodes is conductively coupled to the film. The electrodes are configured for coupling to an electrical measurement device, such as an ohmmeter. Electrical resistance (R), or an analogous electrical characteristic, across the thin film is monitored. Upon exposure to gaseous chemical agents, resistance of the ITO thin film changes. A chemical agent may be identified by a characteristic change in resistance in the presence of test gas or vapor at ambient temperature. Significantly, the sensor operates at ambient temperature without requiring a heater, such as an external or integrated heater.

An exemplary sensor array according to principles of the invention comprises a plurality of ITO thin film sensors formed on an insulator substrate. The sensors share a common electrode. A unique second electrode associated with each sensor enables measurement of electrical resistance (R) across each thin film comprising a sensor. An interface circuit comprising a perforated circuit board mates with the substrate. The circuit board includes apertures to expose the sensors to ambient gas. The circuit board also provides electrically conductive leads to operably couple the electrodes to terminals. The terminals are configured for connection to a cable connector, which may be operably connected to the monitoring equipment.

Referring now to FIG. 1, a perspective view of an exemplary sensor 100 according to principles of the invention is conceptually illustrated. The sensor comprises an indium tin oxide (ITO) thin film 105 in the form of a strip on an electrically insulating substrate 110. A pair of electrically conductive electrodes 115, 120 is electrically coupled to the ITO thin film 105, with one electrode at each opposite end of the thin film 105. The electrodes 115, 120 may be electrically coupled to monitoring equipment configured to measure one or more electrical characteristics of the thin film 105, such as resistance across the film 105, over time. The resistance of the ITO thin film 105 will change over time in an identifiable manner shortly after the thin film is exposed to a particular CWA. Thus, monitoring resistance over time enables determination of the presence of a CWA as well as identification of the CWA. Advantageously, the sensor 100 may be used to identify any CWA for which a characteristic electrical response has been determined.

Figure 2:
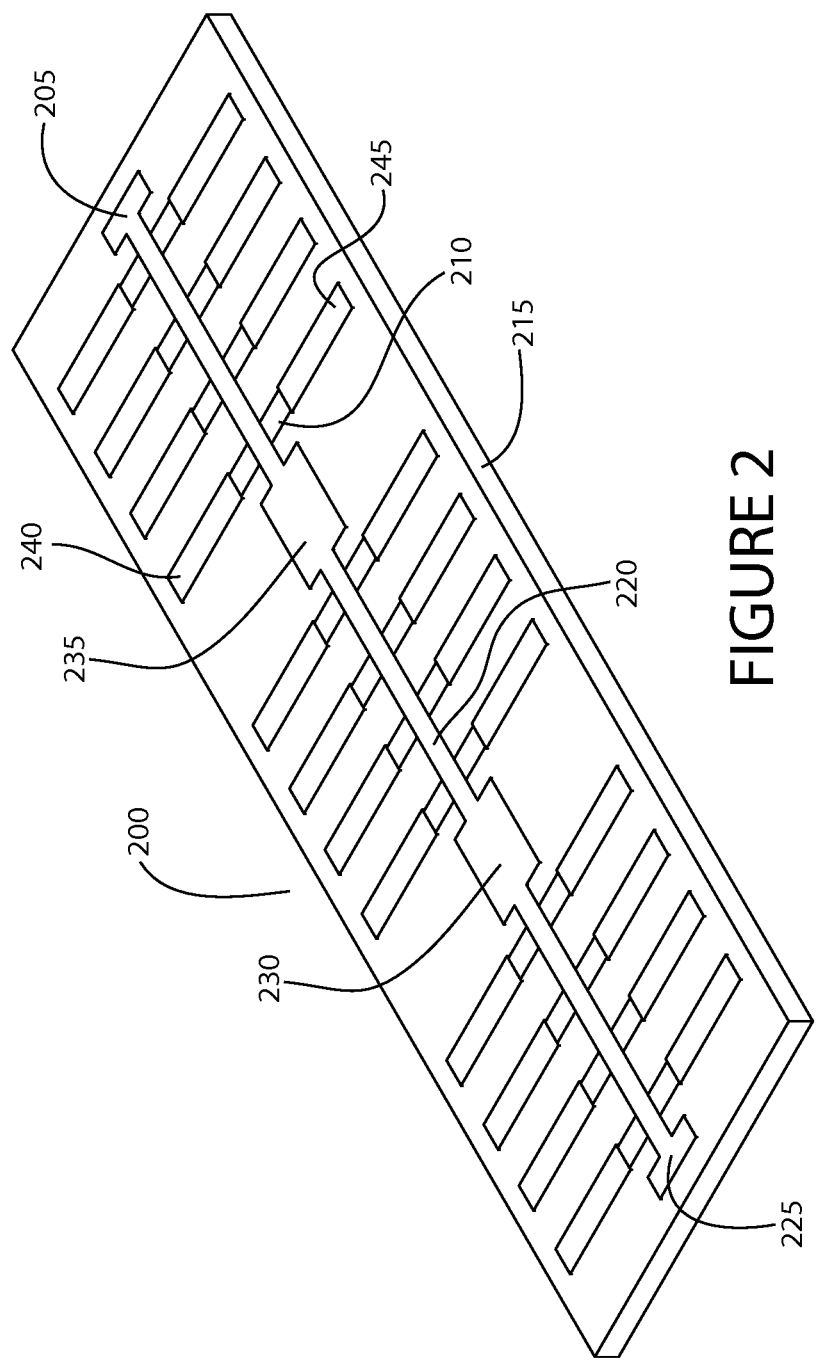
FIG. 2 shows a perspective view of an exemplary sensor slide with a sensor array according to principles of the invention.

FIG. 2 provides a perspective view of an exemplary sensor slide 200 with a sensor array according to principles of the invention. A plurality of ITO thin film sensor strips 210 are formed on an insulator substrate 215. The sensor strips 210 share a common central electrode 220 with several discrete interface pads 205, 225, 230 and 235. The common central electrode 220 is electrically coupled to each sensor strip 210 at approximately the midpoint of the strip 210. An end electrode 240, 245 is operably coupled to each end of each ITO thin film strip 210. Thus, each strip 210 provides two sensors, i.e., two sensible portions. The portion of the strip 210 between the common central electrode 220 and one end electrode 240 constitutes one sensor, while the portion of the strip 210 between the common central electrode 220 and the other electrode 245 constitutes the second sensor. Each sensor is a portion of an ITO thin film strip 210 that can be exposed to a chemical agent and for which electrical resistance can be measured. Interface pads 205, 225, 230 and 235 of the common electrode 220 are portions at which the common electrode 220 may be electrically connected to an interface circuit 300, as discussed below. Similarly, each end electrode 240, 245 is electrically connected to the interface circuit 300, as discussed below.

Figure 3:
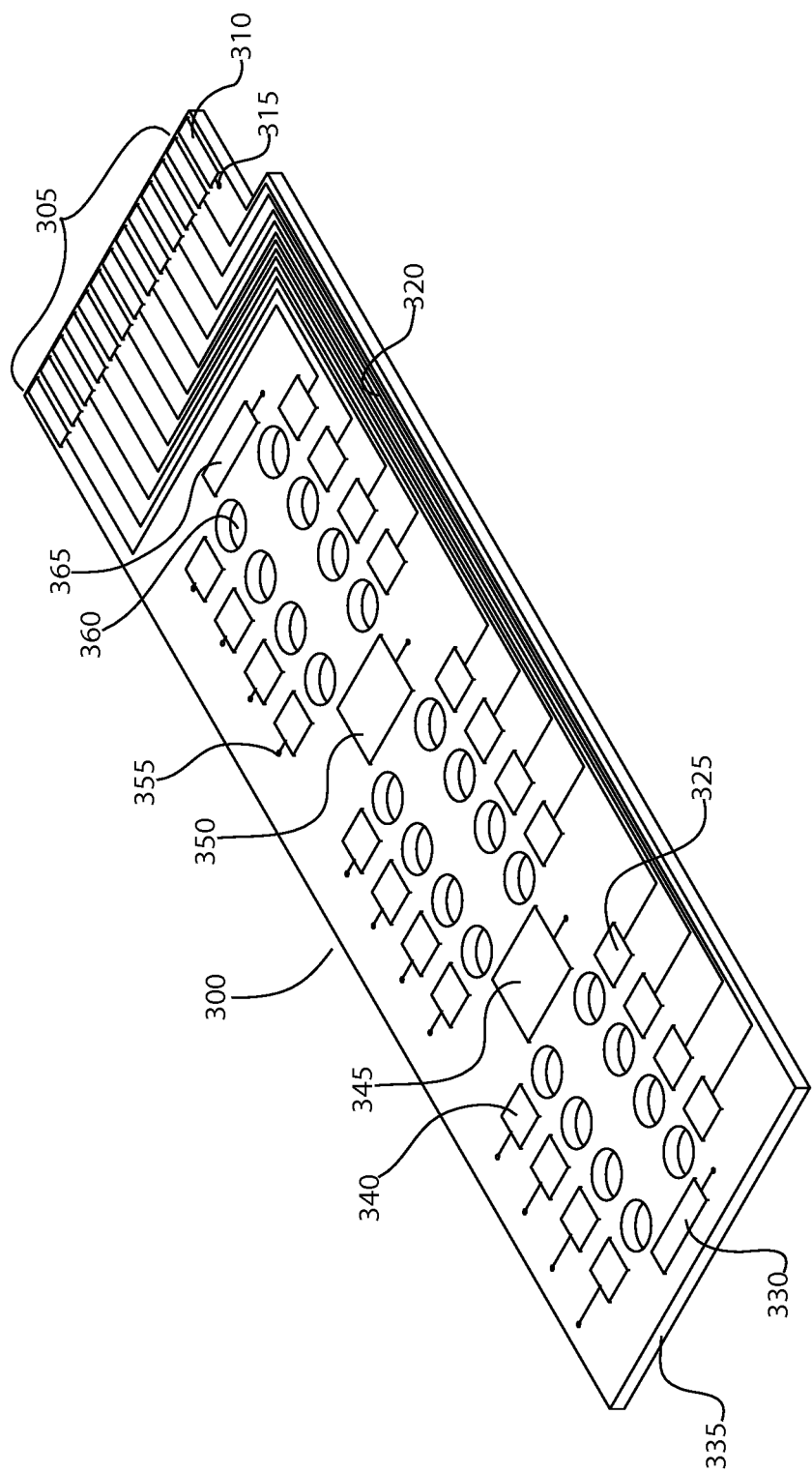
FIG. 3 shows a perspective view of an exemplary printed circuit board interface for a sensor array according to principles of the invention.
Figure 4:
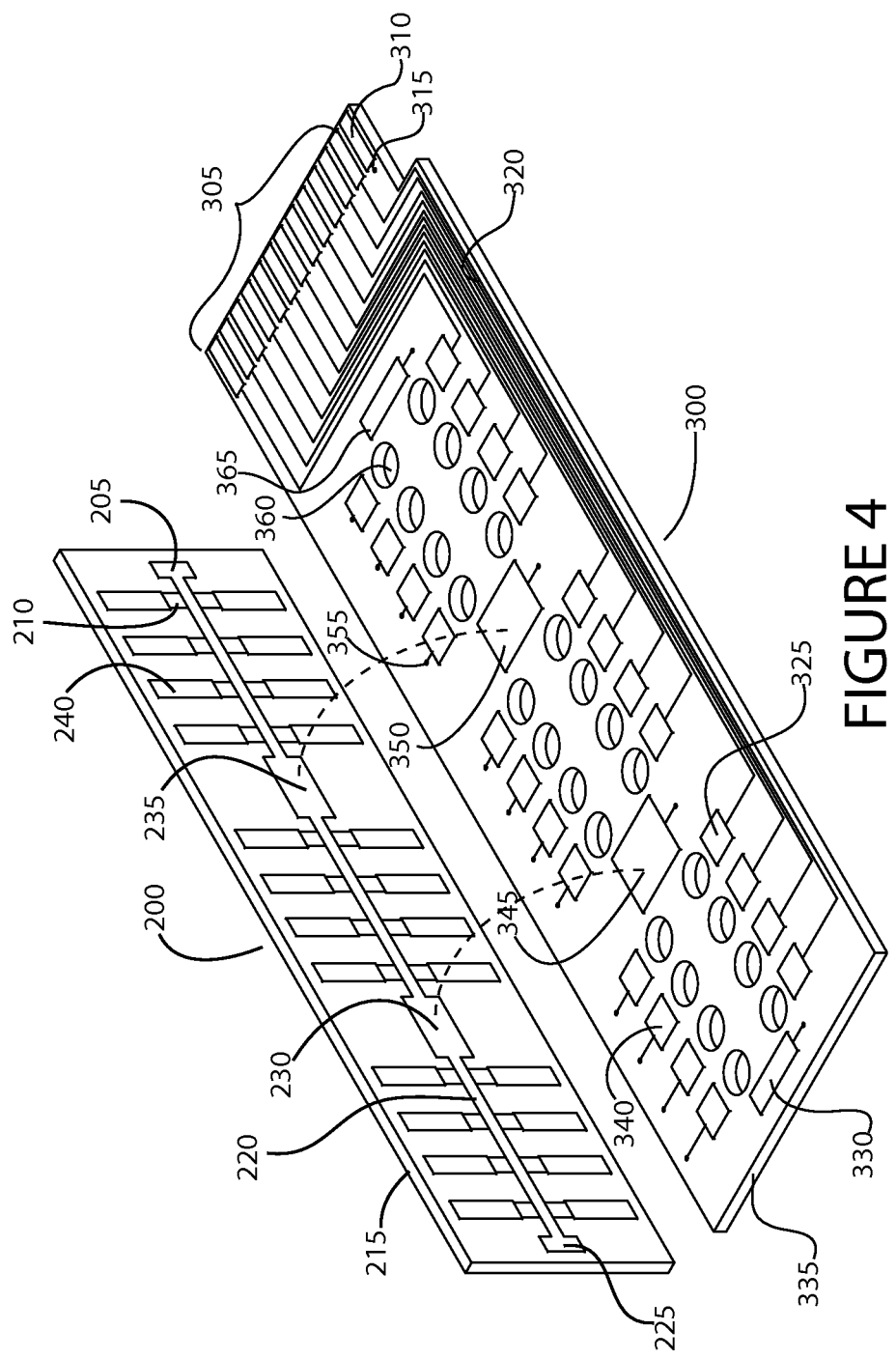
FIG. 4 shows a perspective view of an exemplary sensor slide and an exemplary printed circuit board interface for a sensor array according to principles of the invention.

Referring now to FIG. 3, a perspective view of an exemplary printed circuit board interface (i.e., an interface circuit) 300 for a sensor array according to principles of the invention is provided. The exemplary interface circuit 300 comprises a printed circuit board, or PCB. The PCB features conductive pathways, or traces 320, etched from copper sheets laminated onto a non-conductive PCB substrate 335. The substrate 335 mechanically supports the electrical features. The interface circuit 300 includes a plurality of electrodes 325, 330, 340, 345, 350, 365, configured (i.e., positioned, sized and shaped) to electrically engage the electrodes 240, 245 and pads 205, 225, 230, 235 of the sensor slide 200, when the sensor slide 200 is mounted onto the interface circuit 300, as conceptually illustrated in FIG. 4. Thus, for example, electrode 330 may be electrically coupled to pad 225, while electrode 345 may be electrically coupled to pad 230. Each electrode on the interface circuit 300 is electrically connected to one of a plurality of traces 320, 520, each of which leads to a terminal 305, 505, 310, 510. The sensor slide 200 may be secured to the interface circuit 300 using a mechanical fastener, such as a clamping device, and/or a chemical fastener, such as an adhesive or bonding agent.

Figure 5:
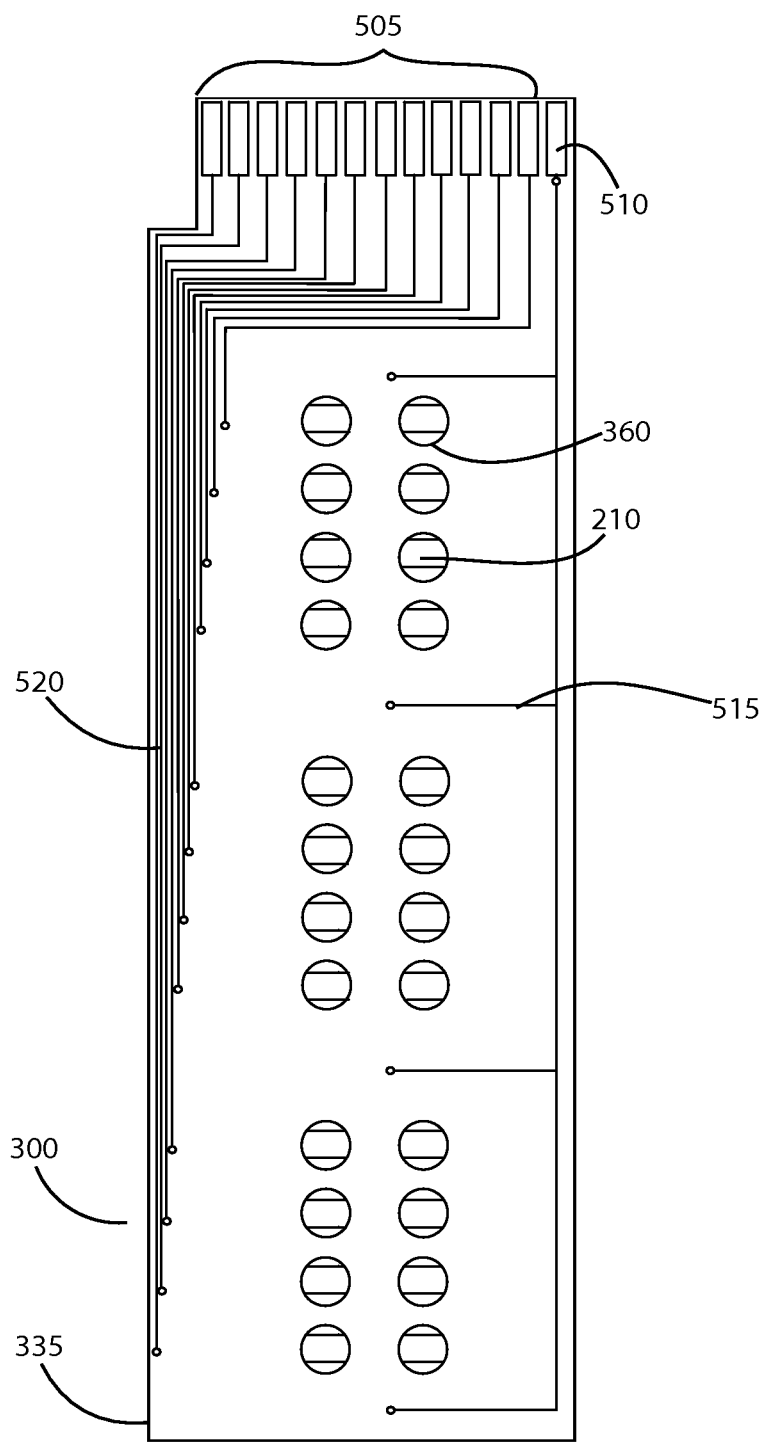
FIG. 5 shows a bottom plan view of an sensor assembly comprising a sensor slide and printed circuit board according to principles of the invention.

The exemplary interface circuit board is two-sided. Holes, or vias 315, 355, are formed through the substrate 335. The walls of the vias 355 are plated with copper to form plated-through holes that electrically connect one side of the PCB with the opposite side. As shown in FIG. 5, traces 515, 520 on the bottom of the interface circuit board 335 lead from vias 355 to terminals 505, 510 on the bottom of the circuit board 335. The bottom terminals 505, 510 and top terminals 305, 310 may be engaged by a PCB card edge connector and wiring harness.

The exemplary interface circuit 300 includes twenty six (26) terminals at an edge, thirteen (13) terminals on one side of an edge of the interface circuit 300, and thirteen terminals on the other side of the edge of the interface circuit 300. Two terminals 310 are connected to traces, which connect to electrodes 330, 345, 350, 365 configured to couple with the pads 205, 225, 230, 235 of the common electrode 220. Each of the remaining twenty four terminals 305 is connected to a trace, which connects to an electrode configured to couple with an end electrode of the sensor slide 200, such as electrode 240 or 245. Thus, each end electrode 240, 245 may be electrically connected to one terminal 305 of the interface circuit 300. Conveniently, the edge mounted terminals 305, 310 may be engaged by a PCB edge connector. The edge connector may be coupled to cables or a wiring harness, which may be connected to measuring and monitoring equipment.

The exemplary interface circuit 300 is perforated. The perforations 360 allow chemical agents to permeate the circuit board 335. As shown in the bottom view of FIG. 5, the perforations are configured (i.e., shaped, positioned and sized) to expose a substantial portion of each ITO thin film strip 210 to the ambient environment when the sensor slide 200 is mounted onto the interface circuit 300. This exposure facilitates rapid sensing of the presence of a chemical agent.

One sensor associated with each end of each sensor enables measurement of electrical resistance (R) across each thin film comprising a sensor. An interface comprising a perforated circuit board mates with the substrate. The circuit board includes apertures to expose the sensors to ambient gas. The circuit board also provides electrically conductive leads to operably couple the electrodes to terminals. The terminals are configured for connection to a PCB edge connector, which may include a wire harness operably connected to the monitoring equipment.

Figure 6:
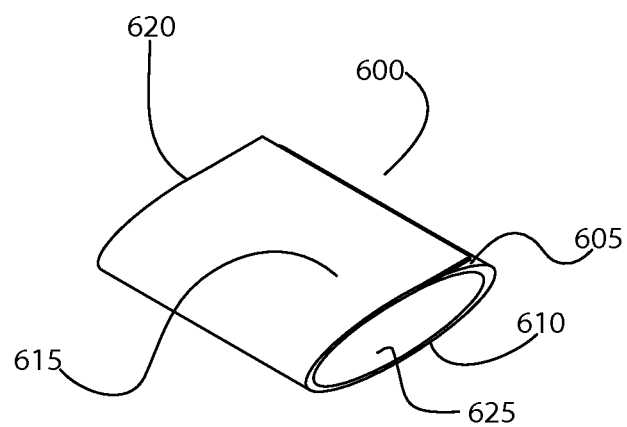
FIG. 6 shows a perspective view of an exemplary conductive tape joint for use in joining a sensor slide to a printed circuit board in accordance with principles of the invention.

FIG. 6 shows an exemplary conductive tape band 600 which may be used to join electrodes of the sensor slide 200 to corresponding electrodes of the printed circuit board interface 300. A band 600 may be sized and configured to conductively join each common electrode 330, 345, 350, 365 to each corresponding pad 205, 225, 230, 235 of the common electrode 220. Likewise, a band 600 may be sized and configured to conductively join each end electrode 240, 245 to a corresponding trace electrode 325 on the printed circuit board interface. The tape comprises a foil (e.g., copper foil) backing and an electrically conductive pressure-sensitive adhesive supplied with a removable liner for easy handling. After the liner is removed, the tape is formed into a ring-like band 600 as shown in FIG. 6. The band includes a top portion 620 and a bottom portion 610. The outer surface 615 of the band 600 includes the adhesive. Because the band includes an overlap 605, the band adheres to itself. An interior compartment 625 thus formed does not include adhesive. Therefore, the top portion 620 of the band 600 may move apart slightly from the bottom portion 610 of the band 600 when urged. When relieved, the top portion 620 of the band 600 may move gradually towards the bottom portion 610 under the influence of gravity. One or more wrappings may be utilized to achieve a determined physical resistance. This construction provides a shock absorbing effect that helps maintain structural integrity of the sensor assembly.

Figure 7:
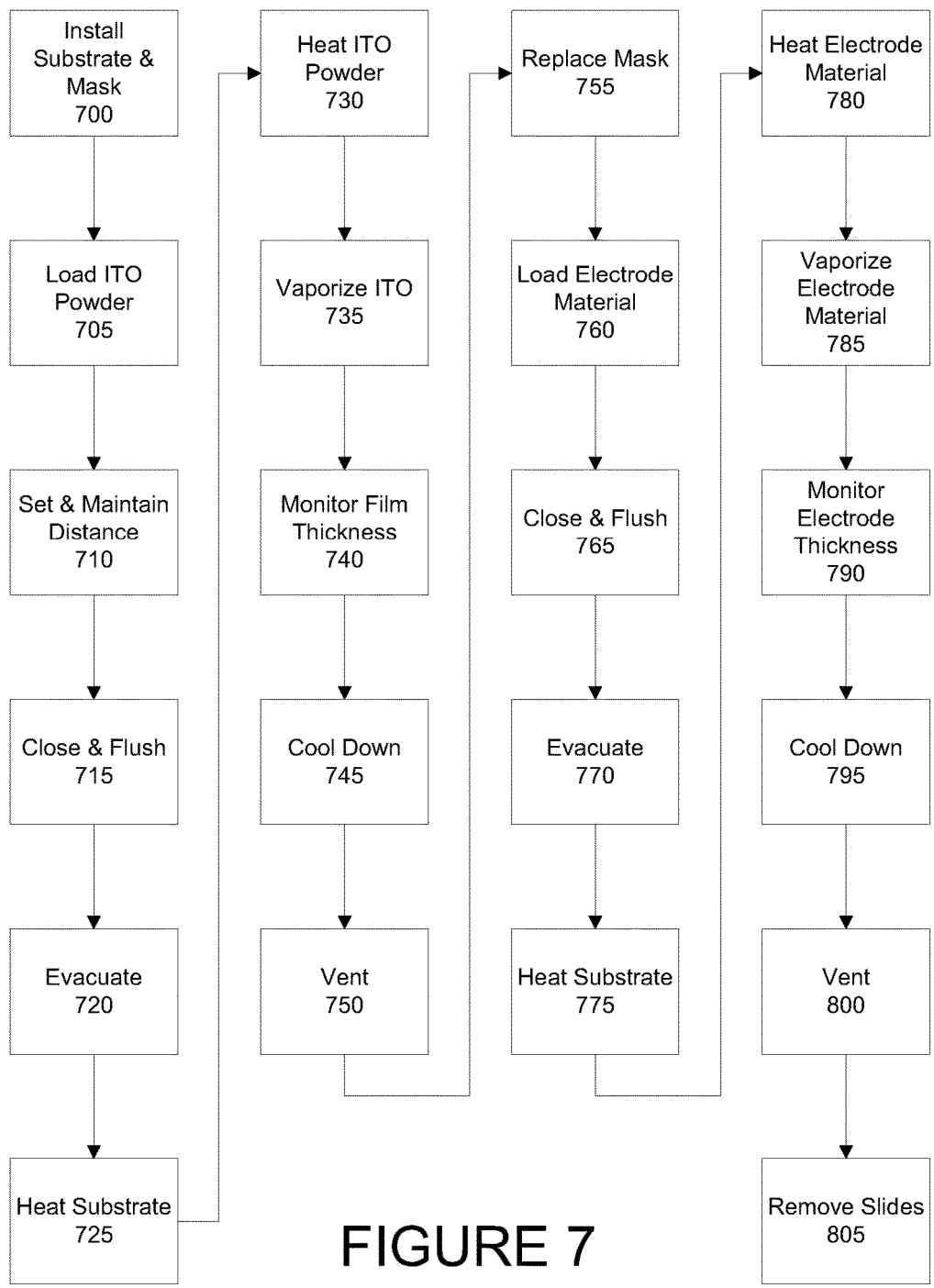
FIG. 7 shows a flowchart for an exemplary process of manufacturing a sensor array in accordance with principles of the invention.

Exemplary sensors according to principles of the invention may be fabricated using any method of forming a uniform ITO thin film on a compatible insulator. By way of example and not limitation, a uniform ITO thin film may be deposited on a substrate via thermal evaporation in a metal box chamber evacuated to approximately the order of $10^{-6}$ torr, as conceptually illustrated in the flowchart of FIG. 7. Turbomolecular high vacuum and rotary pumps are used in series to generate the high vacuum. The substrate and a mask are installed in the chamber on a holder, as in step 700. A determined amount (e.g., 0.2 gram) of the evaporant, i.e., ITO (e.g., 90% indium oxide and 10% tin oxide, percent by weight) (0.2 gram) bulk powder, is loaded in a refractory metal boat or crucible, such as a tantalum (Ta) boat, as in step 705. The distance between the Ta boat and substrate is set and maintained constant (e.g., at about 25 cm), as in step 710.

The substrate is a stratum that does not react with the deposited material and withstands the processing conditions. Cleaned microscope plain glass slides (e.g., Fisher Scientific, 3"×1"×1 mm slide), alumina (e.g., MIT, Inc, fine ground, 1"×1"×1 mm), silicon wafer (e.g., Silicon Quest Inc, 3" diameter, 13-17 mill thickness, orientation <100>, p-type) or other compatible material may be used as the substrate. If a glass slide is used as the substrate, it is preferably cleaned with detergent, deionizer water and acetone using an ultrasonic cleaner and then fully dried in an oven before use. Other materials may be cleaned using similar compatible cleaning steps to remove all potential contaminants.

The mask is stencil or other masking means that limits deposition of the ITO thin film to only determined portions of the substrate. By way of example and not limitation, the mask comprises a refractory metal with a low vapor pressure at the evaporation temperature and low reactivity with the ITO evaporant, such as tungsten (W), titanium (Ti), or molybdenum (Mo), or tantalum (Ta), or stainless steel, or Invar (Nickel Iron Alloy). In an alternative (albeit less efficient) implementation, the ITO thin film may be formed on the entire substrate. Subsequently, a subtractive process, such as etching, may be performed to selectively remove deposited portions from the substrate. A resist and wet (e.g., chemical) or dry (e.g., plasma) etching process may be utilized.

After the substrate, mask and evaporant are properly loaded, the chamber may be closed and flushed with dry nitrogen gas for a determined period of time, 5 minutes, as in step 715. Afterwards, the vacuum system is activated and the chamber is evacuated to the order of $10^{-6}$ torr, as in step 720. Next, a substrate heater is activated and substrate temperature is elevated and maintained at a determined temperature (e.g., 250 to 300° C.) using digital closed loop temperature controller, as in step 725. Next, a power supply for the evaporant boat is activated and current through the boat is slowly increased and then maintained uniform until the boat reaches a determined evaporation temperature (e.g., approximately 700 to 800° C.), as in step 730. Upon reaching the determined evaporation temperature, ITO begins to vaporized and deposit as a thin film on the substrates, as in step 735. A thickness monitor, such as a digital quartz crystal thickness monitor, may be used to determine and monitor the deposition rate and thickness of deposited film, as in step 740. The preferred thickness is approximately 500 to 4000 Å, and preferably 1500 and 2000 Å. After evaporation is complete, the substrate heater may be deactivated and allowed to cool to room temperature, as in step 745. The chamber may then be vented using dry nitrogen gas, as in step 750. At this point in the process, the substrate has been coated with a nanocrystalline ITO thin film of uniform thickness.

After formation of the ITO thin film on the substrate, electrodes are formed over portions thereof. The electrodes may be formed using any suitable fabrication technique. In a preferred implementation, the thermal evaporation process is utilized, in which case, the metal mask for the ITO thin film pattern may be replaced with a metal mask for electrode pattern, as in step 755. Gold foil (0.03 to 0.05 gram) is loaded into a refractory metal boat or crucible made of tungsten (W), as in step 760. Then, the chamber is closed and flushed with dry nitrogen gas for 5 minutes, as in step 765. After flushing, the chamber is evacuated to approximately to the order of $10^{-6}$ torr, as in step 770. The substrate heater may then be activated until the substrate temperature is raised to about 70° C., as in step 775. The power supply of the tungsten boat is activated and the current is slowly raised until the boat turns white hot and reaches a determined evaporation temperature for the gold foil, as in step 780, upon which, the gold foil melts and vaporizes, as in step 785. The gold vapor then deposits on substrates as a thin film. After achieving and monitoring 2500 to 4000 Å thickness of gold film using a thickness monitor, as in step 790, the power supply is turned off, the vacuum is maintained and the system is allowed to cool down, as in step 795. The chamber is then vented and slides having sensors are removed for storage, as in step 800.

In an exemplary embodiment, twenty four (24) sensors are fabricated on one slide and a total of 96 sensors may be fabricated on four (4) glass slides simultaneously in one deposition run. However, the invention is not limited to any particular number of sensors per slide, nor is the invention limited to any particular number of slides per deposition run. Fewer or more than twenty four (24) sensors may be fabricated on a slide in accordance with the principles of the invention. Fewer or more than four (4) sensor slides may be fabricated simultaneously in accordance with the principles of the invention. Additionally slides can be divided, e.g., cut into discrete parts (e.g., 3 parts) so that each part has some (e.g., 8) sensors.

In the exemplary embodiment, each sensor has an active area of about 25 mm×25 mm. However, the invention is not limited to any particular sensor size. Sensors that have a larger or smaller lengths and/or widths may be fabricated on a slide in accordance with the principles of the invention.

The sensors may be configured to work individually or in groups, in parallel or in series. Each sensor may work alone and/or a plurality of sensors (e.g., all 24 sensors in the exemplary embodiment) can work simultaneously in arrays.

Figure 8:
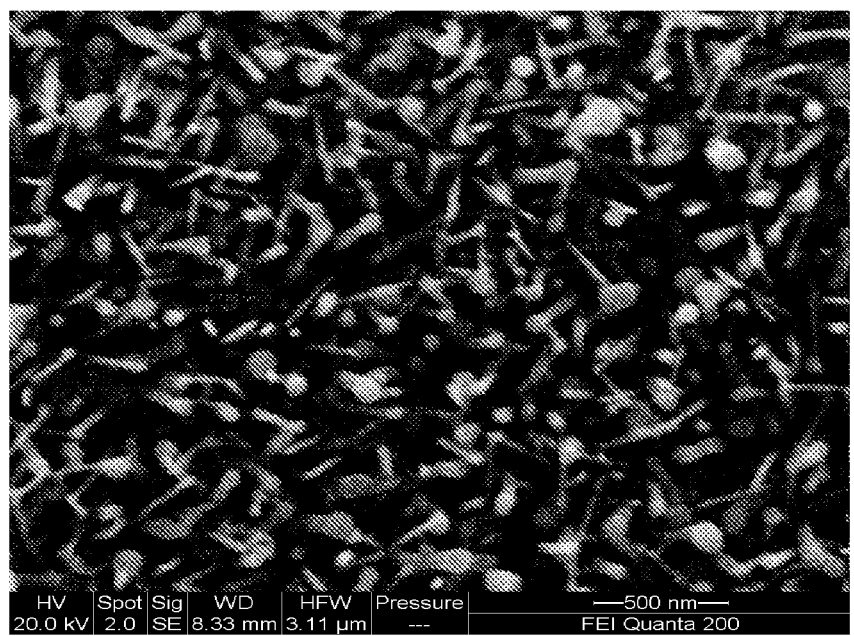
FIG. 8 is an electron micrograph of an exemplary ITO thin film sensor, which reveals an average grain size of approximately 20 to 60 nm (nanometers), in accordance with principles of the invention.

The surface of ITO thin film sensors fabricated using a process as described above were examined using an Environmental Scanning Electron Microscope (ESEM, Quanta 200, FEI). FIG. 8 shows an electron micrograph of ITO thin films sensors, which reveals a nanocrystalline structure with average grain sizes that vary from 20 to 60 nm. This confirmed that ITO films have nanocrystalline structure, which is considered important for sensitivity and response time. Chemical composition of film was determined using energy dispersive analysis of x-rays (EDAX) attached with ESEM.

Tests were conducted to evaluate the response of sensors fabricated in accordance with principles of the invention. A sensor slide having 24 sensors was mounted to an interface PCB as described above. The assembly was kept in a glass jar (500 ml, Chase Scientific Glass, Inc or Fisher Scientific) having an air tight lid. A flat ribbon cable with a 25-pin PCB edge connector was attached to the lid, with the cables being allowed to pass through the lid. The glass jar was placed in a hood during tests. In the case of a liquid chemical agent, a known amount of test liquid was injected into the closed glass jar using a syringe. In the case of a gaseous chemical agent a known amount of test chemical in gas form was injected by a gas-tight syringe. In the case of a liquid, the liquid was not applied to the sensor and the sensor did not come into contact with the liquid during injection of the chemical agent. Instead, only the resultant vapor from the liquid contacted the sensor. Two terminals of the sensor assembly were connected to an electrometer via a flat cable. Then, the glass jar was flushed with dry nitrogen gas in order to remove any residual air and moisture from the glass jar. After stabilizing baseline, the electrical resistance of the sensor was measured before injecting test chemicals. The value of this resistance was labeled as "Ra". Then, the test chemical was injected. After stabilizing, change in resistance of sensors was measured. This value of resistance was labeled as "Rg". The ITO thin film gas sensors were tested and calibrated at room temperature. After each test run, the used syringe, used glass jar, used lid and sensor assembly were thoroughly neutralized with chemicals and then properly disposed. The concentration of liquid agents, e.g., GD, HD and VX, was determined using a mass spectrometer attached to a gas chromatograph. The concentration of gaseous agents, e.g., CG, was calculated based on the known amount of injected gas relative to the volume of the jar.

Chemical agents that have the ability to oxidize other substances (e.g., an ITO sensor) are said to be oxidative and are known as oxidizing agents, oxidants or oxidizers. The oxidizing agent removes electrons from another substance, and is thus reduced itself. In the presence of oxidizing test chemicals, the resistance of the sensor increased.

Chemical agents that have the ability to reduce other substances (e.g., an ITO sensor) are said to be reductive and are known as reducing agents, reductants, or reducers. The reducing agent transfers electrons to another substance, and is thus oxidized itself. In the presence of reducing test chemicals, the resistance of the sensor decreased, while in the presence of oxidizing test chemicals, the resistance of sensor increased.

Figure 9:
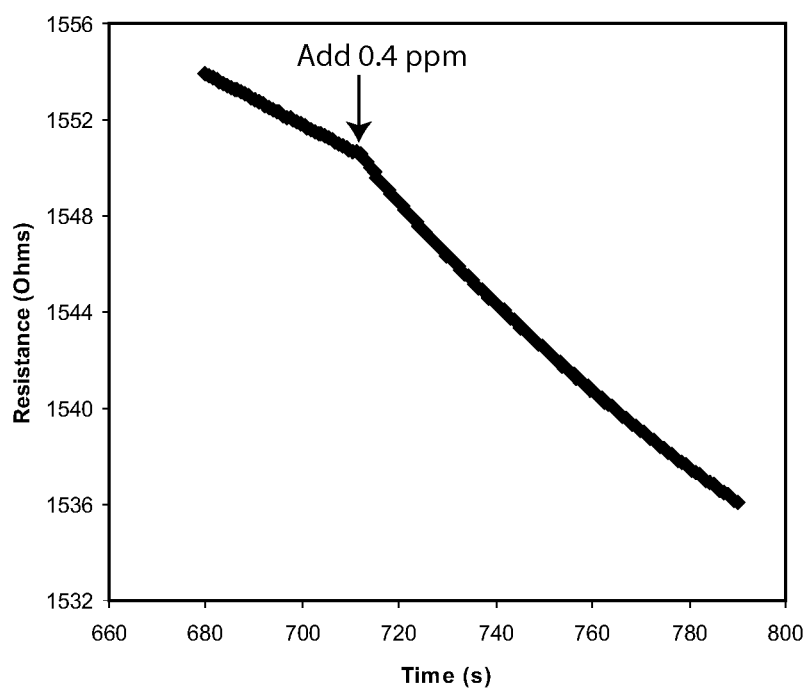
FIG. 9 is a chart that illustrates the response of an ITO sensor according to principles of the invention in the presence of phosgene gas having a concentration of 0.4 ppm (parts per million)

The response of a thin film nanocrystalline ITO sensor assembly according to principles of the invention exposed to phosgene gas (CG) at a concentration of 0.4 ppm is shown in FIG. 9. The thickness of the ITO film was about 1500 Å and the film was fabricated at about a 300° C. substrate temperature. The sensors responded rapidly, with an appreciable change in resistance occurring in about 60 to 80 seconds.

Figure 10:
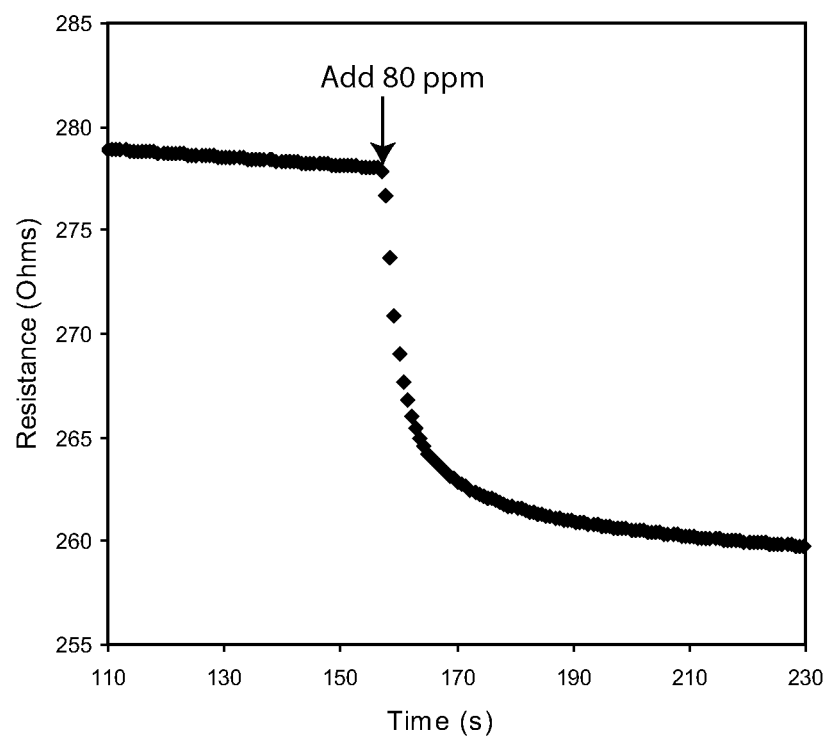
FIG. 10 is a chart that illustrates the response of an ITO sensor according to principles of the invention in the presence of phosgene gas having a concentration of 80 ppm.

The response of a thin film nanocrystalline ITO sensor assembly according to principles of the invention exposed to phosgene gas (CG) at a concentration of 80 ppm is shown in FIG. 10. The thickness of ITO film was about 2000 Å and the film was fabricated at about a 300° C. substrate temperature. The sensors responded rapidly, with an appreciable change in resistance occurring in about 1 second.

A % sensitivity of a sensor was determined by the following equation:

$$\% \text{ Sensitivity} = g = \frac{(R_a - R_g)}{R_g} \times 100$$

where:
$R_a$=Resistance of sensor measured in the absence of test gas or chemicals; and
$R_g$=Resistance of sensor measured in the presence of test gas or chemicals.

Figure 11:
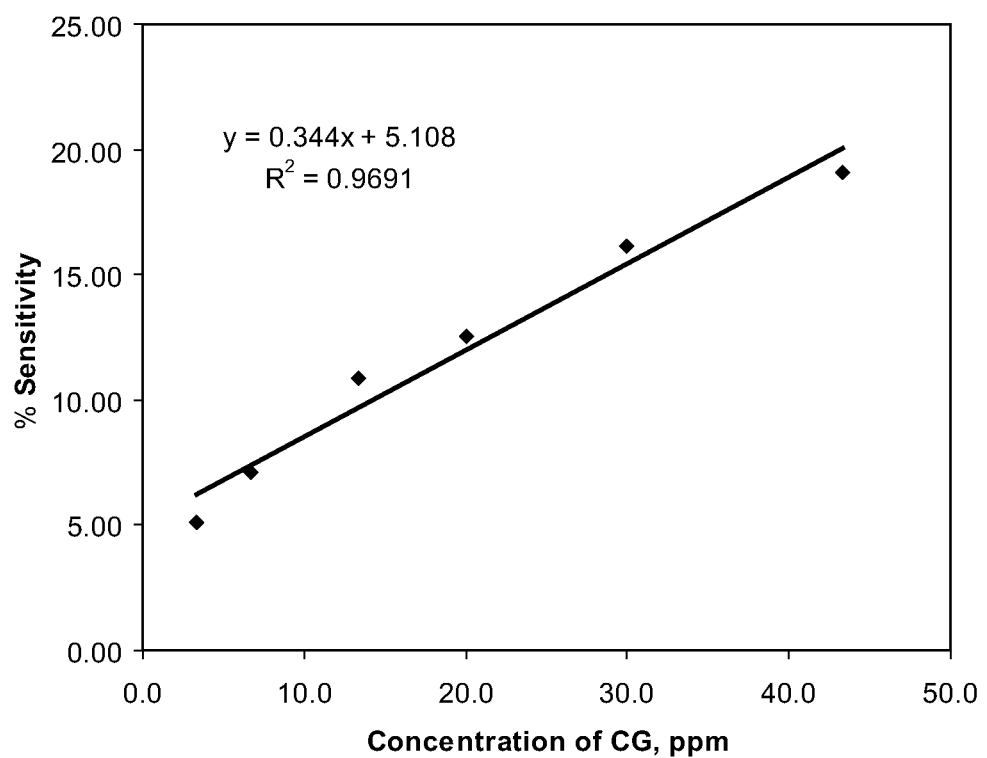
FIG. 11 is a chart that illustrates calibration of an ITO thin film sensor having a thickness of 1500 Å in the presence of phosgene in accordance with principles of the invention.

A calibration of ITO sensors with variation of concentration of CG up to 42 ppm is shown in the FIG. 11. The thickness of ITO film was about 1500 Å and the film was deposited at approximately a 300° C. substrate temperature. The measured response data fit nearly linearly with a correlation coefficient $(R^2)$=0.9691, which indicates the strength and direction of a linear (or a nearly linear) relationship between % sensitivity and concentration. The slope of the plot is 0.344%/ppm.

Figure 12:
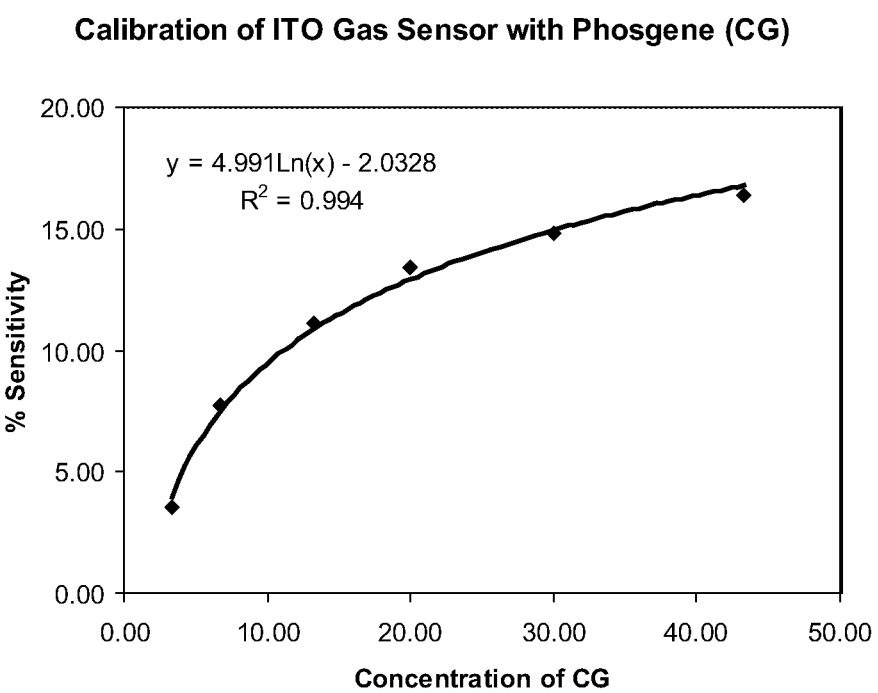
FIG. 12 is a chart that illustrates calibration of an ITO thin film sensor having a thickness of 2000 Å in the presence of phosgene in accordance with principles of the invention.

Another calibration of ITO sensors with variation of concentration of CG up to 42 ppm is shown in FIG. 12. The thickness of ITO film was about 2000 Å and the film was deposited at approximately a 300° C. substrate temperature. The measured response data fit substantially into a log function with a correlation coefficient $(R^2)$=0.994. It was deduced that calibration of ITO sensors having a film thickness of about 1500 Å is nearly linear, while that of ITO sensors having a film thickness of about 2000 Å is not, for CG gas.

Figure 13:
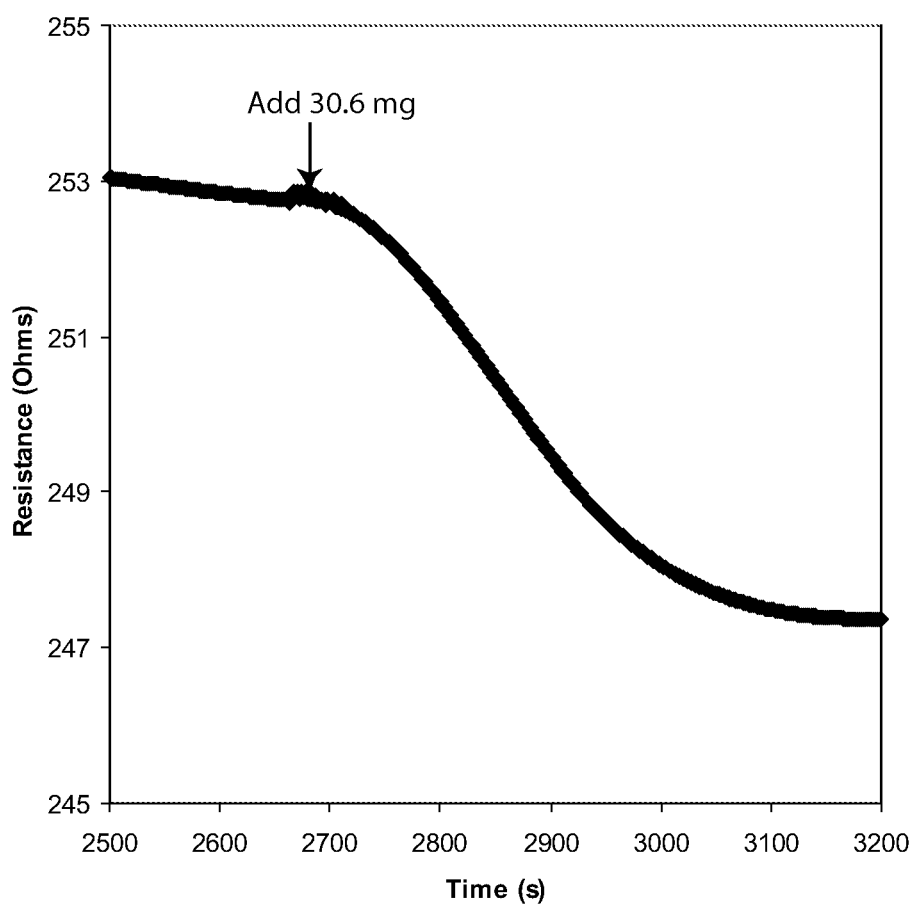
FIG. 13 is a chart that illustrates the response of an ITO sensor according to principles of the invention in the presence of vapor from a liquid form of soman.

The response of a thin film nanocrystalline ITO sensor assembly according to principles of the invention exposed to vapor from liquid soman (GD) is shown in FIG. 13. The thickness of ITO film was about 2000 Å and the film was deposited at approximately a 300° C. substrate temperature. Resistance across a sensor decreased within the response time of nearly 3 to 4 minutes in the presence of GD vapors. The response time can be reduced to the order of seconds if the liquid form of the chemical is converted into vapor by applying external heat to the test liquid form of chemical agent.

The calibration of ITO gas sensors with variation of concentration of GD is shown in the FIG. 14. The thickness of ITO film was about 2000 Å and the film was deposited at approximately a 300° C. substrate temperature. The response is linear (or nearly linear) with a correlation coefficient ($R^2$)=0.9874. The slope of the plot is 0.0002%/ppm.

Figure 15:
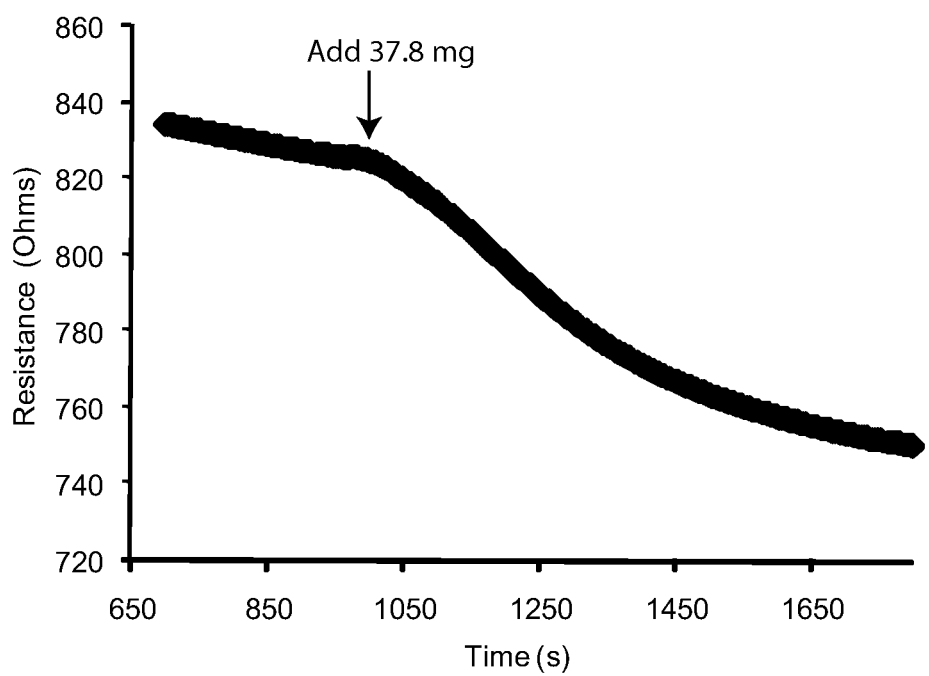
FIG. 15 is a chart that illustrates the response of an ITO sensor according to principles of the invention in the presence of vapor from a liquid form of mustard.

The response of a thin film nanocrystalline ITO sensor assembly according to principles of the invention exposed to vapor from liquid mustard (HD) is shown in FIG. 15. The thickness of ITO film was about 1500 Å and the film was deposited at approximately a 300° C. substrate temperature. Resistance across a sensor decreased within the response time of nearly 4 to 5 minutes in the presence of HD vapors. The response time can be reduced to the order of seconds if the liquid form of the chemical is converted into vapor by applying external heat to the test liquid form of chemical agent.

Figure 16:
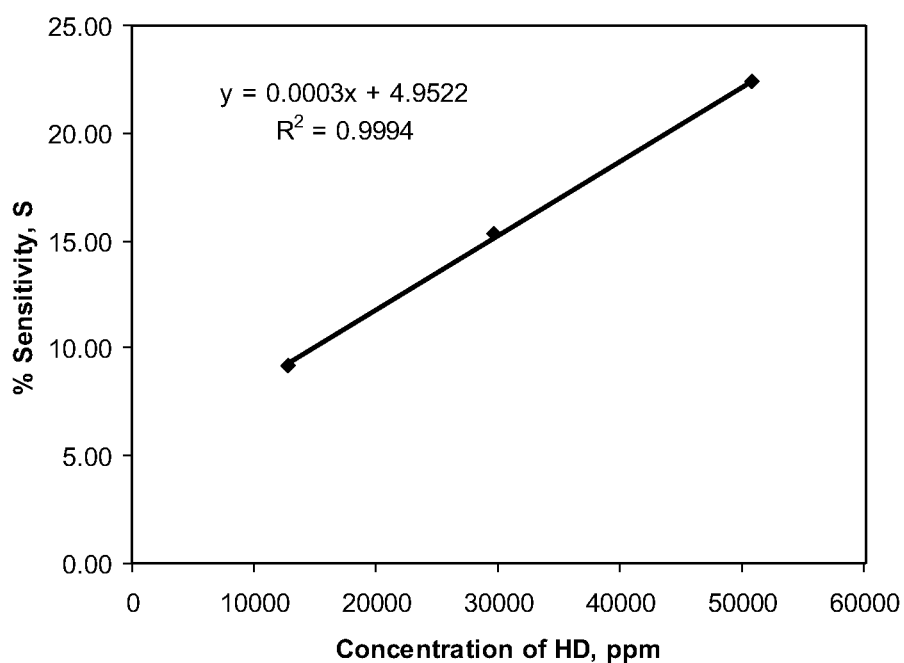
FIG. 16 is a chart that illustrates calibration of an ITO thin film sensor having a thickness of 1500 Å in the presence of liquid form of mustard in accordance with principles of the invention.

The calibration of ITO gas sensors with variation of concentration of HD is shown in FIG. 16. The thickness of ITO film was 1500 Å and the film was deposited at a 300° C. substrate temperature. The response is linear (or nearly linear) with a correlation coefficient ($R^2$)=0.9994. The slope of the plot is 0.0003%/ppm.

Figure 17:
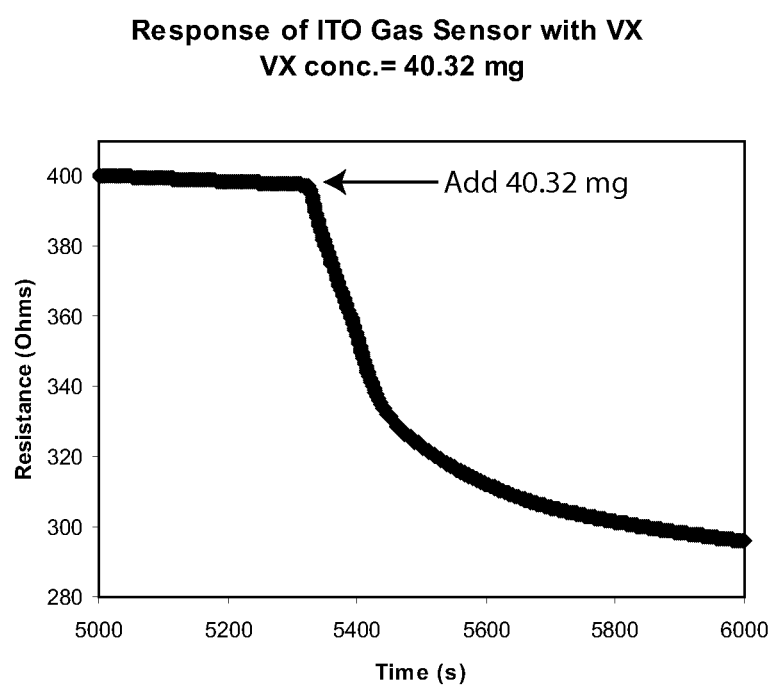
FIG. 17 is a chart that illustrates the response of an ITO sensor according to principles of the invention in the presence of vapor from a liquid form of VX.

The response of a thin film nanocrystalline ITO sensor assembly according to principles of the invention exposed to vapors from VX at a concentration of 40.32 mg is shown in FIG. 17. The thickness of ITO film was 1500 Å and the film was deposited at a 250° C. substrate temperature. The resistance of the sensor appreciably decreased within a response time of approximately 2 to 3 minutes in the presence of VX.

The calibration of ITO gas sensors with variation of concentration of VX is shown in FIG. 18. The thickness of ITO film was 1500 Å and the film was deposited at a 250° C. substrate temperature. The response is linear (or nearly linear) with a correlation coefficient ($R^2$)=0.9943. The slope of the plot is 0.0008%/ppm.

Figure 19:
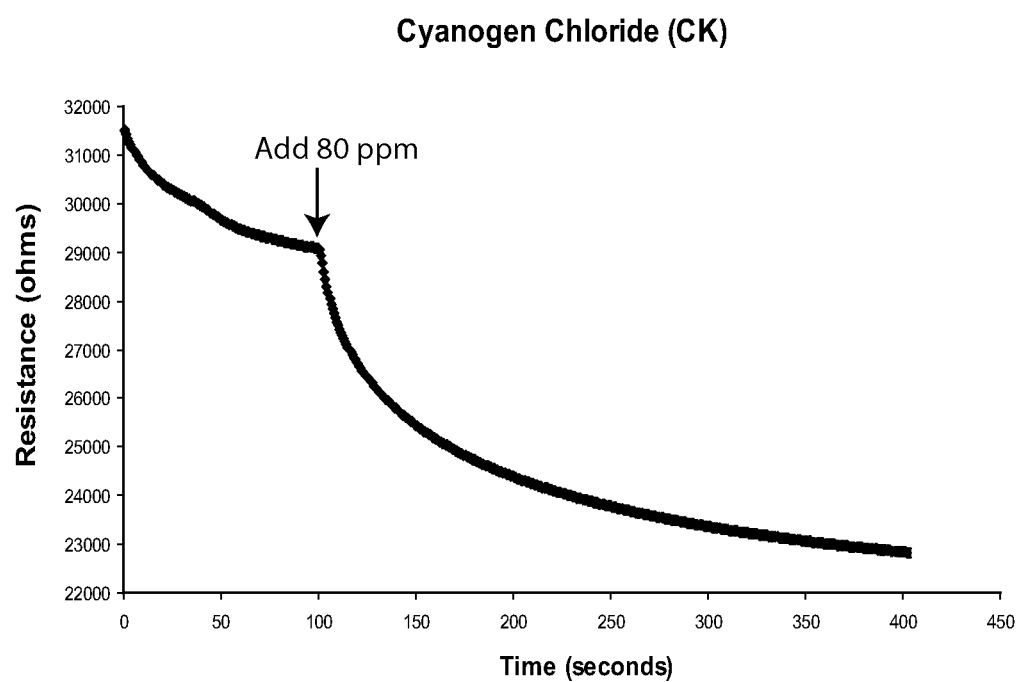
FIG. 19 is a chart that illustrates the response of an ITO sensor according to principles of the invention in the presence of cyanogen chloride gas.

The response of a thin film nanocrystalline ITO sensor assembly according to principles of the invention exposed to cyanogen chloride (CK) gas at a concentration of 80 ppm is shown in FIG. 19. The CK gas was injected in the container using a Polyvinyl fluoride (PVF) Tedlar® (Dupont) bag. The response time is about 80 to 100 seconds. CK is blood agent. Cyanogen chloride, like hydrogen cyanide, is a colorless, highly volatile, fast acting, water soluble, and non-persistent agent. The gaseous cyanogen chloride is heavier than air and very irritating to the eyes and mucus membranes of an individual. This agent deprives the blood and organs of oxygen.

Figure 20:
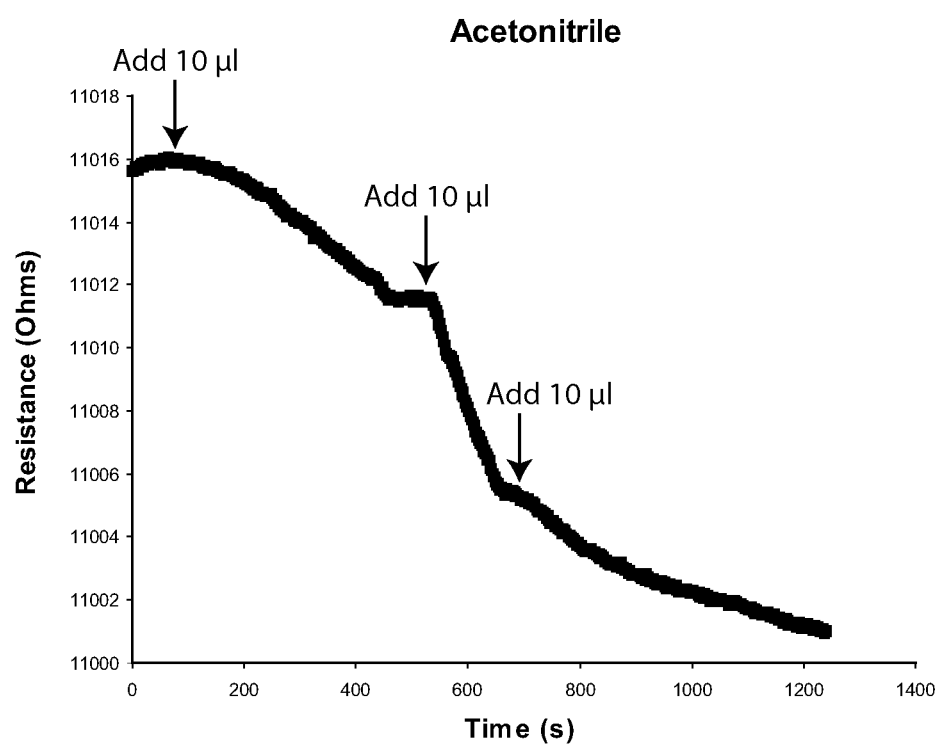
FIG. 20 is a chart that illustrates the response of an ITO sensor according to principles of the invention in the presence of acetonitrile vapor.

The response of a thin film nanocrystalline ITO sensor assembly according to principles of the invention exposed to liquid acetonitrile is shown in FIG. 20. Acetonitrile ($CH_3CN$), also known as Methyl Cyanide or Cyanomethane, is a colorless liquid and an industrial toxic chemical. Three separate 10 µl doses of the test liquid were injected during the test as shown in the chart of FIG. 20.

Figure 21:
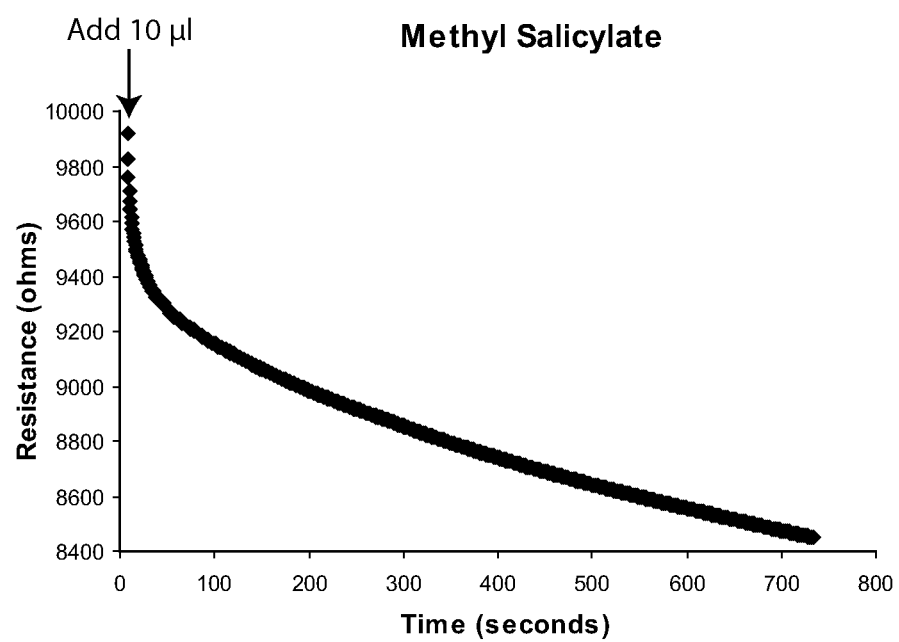
FIG. 21 is a chart that illustrates the response of an ITO sensor according to principles of the invention in the presence of methyl salicylate vapor.

The response of a thin film nanocrystalline ITO sensor assembly according to principles of the invention exposed to liquid methyl salicylate is shown in FIG. 21. Methyl salicylate (chemical formula $C_6H_4(HO)COOCH_3$; also known as salicylic acid methyl ester, oil of wintergreen, betula oil, methyl-2-hydroxybenzoate) is toxic in pure form, especially when ingested. It is also a stimulant of mustard gas.

In operation, a sensor array assembly according to principles of the invention may be utilized to detect and identify specific chemical agents at ambient temperature by comparing changes in electrical resistance of sensors when they are exposed to an environment with determined changes in electrical resistance characteristic of specific chemicals. If the comparison reveals a match, then a chemical agent is detected. If a change in resistance does not match any of the predetermined changes in electrical resistance characteristic of specific chemicals, then an untested chemical agent may be present in the environment. If the resistance remains constant, then the environment has not been contaminated with a determined chemical agent.

A sensor and sensor array according to principles of the invention may be used to detect any chemicals that cause the nanocrystalline ITO thin film to experience a change in resistance. By way of example and not limitation, such chemicals may include ozone, carbon monoxide, carbon dioxide, acetylene, propane, ammonia, sulfur dioxide, ethanol, methanol, volatile organic compounds, industrial toxic chemicals, such as Chloropicrin (PS), Dimethyl Methyphosphonate (DMMP), 1- and 2-proponal, Thioxande, Triethanolamine as well as chemical warfare agents, including those identified above.

In an exemplary implementation, instrumentation operably coupled to a sensor array assembly to perform the method described above includes means for receiving resistance signals, converting the signals to digital resistance data, storing and retrieving digital resistance data characteristic of determined chemical agents, comparing the digital resistance data for the sensed chemical agent with data stored for determined chemical agents, and generating a signal as an alarm if a comparison reveals a match. By way of example and not limitation, such instrumentation may include an analog to digital converter adapted to convert resistance signals into digital resistance data. One or more storage devices, such as volatile and/or non-volatile memory, magnetic disc storage and/or optical disc storage may be provided to store the data. A microprocessor, microcontroller, application specific circuit or other processing device, now known or hereafter developed, may be adapted to perform the comparison and generate a signal. The aforementioned instrumentation is typically included in personal computers equipped with a data acquisition board or peripheral. However, the invention is not limited to any particular instrumentation.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A sensor array for sensing gaseous chemicals, said sensor array comprising:
   a sensor slide comprising
      a slide substrate;

a plurality of nanocrystalline ITO thin film strips formed on said slide substrate, each nanocrystalline ITO thin film strip spaced apart from each other on the slide substrate and each nanocrystalline ITO thin film strip having a first end and a second end separated by the nanocrystalline ITO thin film strip, and wherein, for each of the plurality of nanocrystalline ITO thin film strips, an electrical resistance of said nanocrystalline ITO thin film strip decreases when the nanocrystalline ITO thin film strip is exposed to a sensible gaseous chemical comprising a reducing agent and the electrical resistance of the nanocrystalline ITO thin film strip increases when the nanocrystalline ITO thin film strip is exposed to a sensible gaseous chemical comprising an oxidizing agent;

a common electrode electrically coupled to each of the plurality of ITO thin film strips at approximately the midpoint of each of the plurality of nanocrystalline ITO thin film strips;

a plurality of discrete electrodes, one of each of the plurality of discrete electrodes electrically coupled to the first end of each of the plurality of nanocrystalline ITO thin film strips and one of each of the plurality of discrete electrodes electrically coupled to the second end of each of the plurality of nanocrystalline ITO thin film strips, thereby forming a first sensor portion of the nanocrystalline ITO thin film strip between each of the plurality of discrete electrodes at the first end of each of the plurality of nanocrystalline ITO thin film strips and the common electrode and forming a second sensor portion between each of the plurality of discrete electrodes at the second end of each of the plurality of nanocrystalline ITO thin film strips and the common electrode, and wherein said common electrode and said plurality of discrete electrodes are coupled to an electrical resistance measurement device configured to measure the change in electrical resistance across the first sensor portion and the second sensor portion of each of the plurality of nanocrystalline ITO thin film strips when the sensor array is exposed to a sensible gaseous chemical; and an interface circuit comprising
a circuit substrate;
at least one conductive common electrode pad and a common electrode terminal, the at least one conductive common electrode pad being associated with and electrically coupled to the common electrode terminal;
a plurality of conductive discrete electrode pads and a plurality of discrete electrode terminals, each of said plurality of conductive discrete electrode pads being associated with and electrically coupled to one of said plurality of discrete electrode terminals;
said interface circuit being configured to abut and electrically couple to said sensor slide, with a conductive common electrode pad associated with and electrically coupling to each of said plurality of discrete electrodes of said sensor slide, and the at least one conductive common electrode pad associated with and electrically coupling to the common electrode of said sensor slide.

2. A sensor array for sensing gaseous chemicals according to claim 1, said interface circuit being perforated with a plurality of apertures, each of the plurality of apertures being configured to align with one of the plurality of spaced apart nanocrystalline ITO thin film strips formed on said slide substrate when the interface circuit abuts and electrically couples to said sensor slide.

3. A sensor array for sensing gaseous chemicals according to claim 1, a plurality of conductive tape bands, a conductive tape band being disposed between and configured to adhesively and conductively join each of said plurality of discrete electrodes of said sensor slide and said conductive common electrode pad associated with and electrically coupled thereto.

4. A sensor array for sensing gaseous chemicals according to claim 1, a plurality of conductive tape bands, each conductive tape band including a conductively adhesive outer surface and a non-adhesive inner surface, and each conductive tape band being configured to absorb energy of sudden impulses, a conductive tape band being disposed between and configured to adhesively and conductively join each of said plurality of discrete electrodes of said sensor slide and said conductive common electrode pad associated with and electrically coupled thereto.

5. A sensor array for sensing gaseous chemicals according to claim 1, said interface circuit being a printed circuit board.

6. A sensor array for sensing gaseous chemicals according to claim 1, said slide substrate comprising a material from the group consisting of glass, alumina, silicon, and silicon dioxide.

7. A sensor array for sensing gaseous chemicals according to claim 1,
said slide substrate comprising a material from the group consisting of glass, alumina, silicon, and silicon dioxide; and
said common electrode comprising gold; and
said plurality of discrete electrodes comprising gold.

8. A sensor array for sensing gaseous chemicals according to claim 1, each of said plurality of nanocrystalline ITO thin film strips comprising nanocrystalline ITO thin film having a thickness of 500 to 4000 Å.

9. A sensor array for sensing gaseous chemicals according to claim 1, each of said plurality of spaced apart nanocrystalline ITO thin film strips comprising nanocrystalline ITO thin film having an average grain size of 20 to 80 nm.

10. A sensor array for sensing gaseous chemicals according to claim 1, wherein said electrical resistance measurement device is configured to monitor the electrical resistance across the first sensor portion and the second sensor portion of each of the plurality of nanocrystalline ITO thin film strips over time.

11. A sensor array for sensing gaseous chemicals according to claim 1, said plurality of nanocrystalline ITO thin film strips configured to experience a determined change in the electrical resistance in a determined amount of time after exposure to a gaseous chemical warfare agent.

12. A sensor array for sensing gaseous chemicals according to claim 1, said plurality of nanocrystalline ITO thin film strips configured to experience a determined change in electrical resistance in a determined amount of time after exposure to vapor from a chemical warfare agent.

13. A sensor array for sensing gaseous chemicals according to claim 1, wherein at least one of said plurality of nanocrystalline ITO thin film strips experiences a change in electrical resistance upon exposure to a chemical from the group consisting of
1,2,2-Trimethylpropyl methylphosphonofluoridate (soman, GD),
0-Ethyl S-(2-isopropylaminoethyl) methylphosphonothiolate (VX),
distilled bis (2-chloroethyl) sulfide (mustard, HD), Phosgene (CG), cyanogen chloride (CK),
ozone,
carbon monoxide,
carbon dioxide,
acetylene,
propane,
ammonia,
sulfur dioxide,
ethanol,
methanol,
Chloropicrin (PS),
Dimethyl Methyphosphonate (DMMP),
1- and 2-proponal,
Thioxande, and
Triethanolamine.

* * * * *

UNITED STATES PATENT AND TRADEMARK OFFICE
CERTIFICATE OF CORRECTION

PATENT NO. : 9,606,078 B2  Page 1 of 1
APPLICATION NO. : 11/938290
DATED : March 28, 2017
INVENTOR(S) : Nirmalkumar G. Patel It is certified that error appears in the above-identified patent and that said Letters Patent is hereby corrected as shown below:

On the Title Page

Item (54) and in the Specification, Column 1, Lines 1-2 title should read:
NANOCRYSTALLINE INDIUM TIN OXIDE SENSORS AND ARRAYS In the Claims Column 14, Claim 9, Line 39 should read:
to claim 1, each of said plurality of nancrys- Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*